United States Patent
Dzwiniel et al.

(10) Patent No.: US 10,556,917 B1
(45) Date of Patent: Feb. 11, 2020

(54) METHOD FOR PREPARING BIS-(SILYLALKYL)CARBONATE ESTERS

(71) Applicant: UCHICAGO ARGONNE, LLC, Chicago, IL (US)

(72) Inventors: Trevor L. Dzwiniel, Carol Stream, IL (US); Krzysztof Pupek, Plainfield, IL (US)

(73) Assignee: UCHICAGO ARGONNE, LLC, Chicago, IL (US)

(*) Notice: Subject to any disclaimer, the term of this patent is extended or adjusted under 35 U.S.C. 154(b) by 0 days.

(21) Appl. No.: 16/508,550

(22) Filed: Jul. 11, 2019

(51) Int. Cl.
C07F 7/08 (2006.01)
B01J 31/02 (2006.01)
C07F 7/00 (2006.01)
C07F 7/02 (2006.01)

(52) U.S. Cl.
CPC ........... C07F 7/083 (2013.01); B01J 31/0251 (2013.01); C07F 7/00 (2013.01); C07F 7/02 (2013.01); C07F 7/08 (2013.01); C07F 7/0803 (2013.01); C07F 7/0825 (2013.01)

(58) Field of Classification Search
CPC ...... C07F 7/00; C07F 7/02; C07F 7/08; C07F 7/083; C07F 7/0803; C07F 7/0825; B01J 31/0251
See application file for complete search history.

(56) References Cited

U.S. PATENT DOCUMENTS

2007/0048260 A1  3/2007  Novak et al.
2017/0301953 A1  10/2017  Pena Hueso et al.

FOREIGN PATENT DOCUMENTS

JP  10-172610 A  6/1998
JP  2019133895  *  8/2019  ........... C07C 7/0803

OTHER PUBLICATIONS

Sheludyakov et al., Synthesis and reactions of silicon-containing esters of carbonic acid, Zhurnal Obshchei Khimii (1973), 43(2), 314-20, abstract only.*
Jow, T.R. et al. (eds), Electrolytes for Lithium and Lithium-Ion Batteries, Nonaqueous Electrolytes and Advances in Additives, Chapter 3, 167-190 (2014).
Krumdick, G., Battery Materials Scale-Up and Manufacturing Research, Getting Materials From Discovery to Production, Battery Congress 2017, 1-34, May 10, 2017.
Krumdick, G., Battery Materials Scale-Up and Manufacturing Research, Getting Materials From Discovery to Production, International Battery Seminar, 1-30, Mar. 23, 2017.
Long, B.R. et al., Enabling High-Energy, High-Voltage Lithium-Ion Cells: Standardization of Coin-Cell Assembly, Electrochemical Testing, and Evaluation of Full Cells, Journal of the Electrochemical Society, 163 (14), A2999-A3009 (2016).

* cited by examiner

*Primary Examiner* — Jafar F Parsa
(74) *Attorney, Agent, or Firm* — Olson & Cepuritis, Ltd.

(57) ABSTRACT

Carbonate esters of Formula (I): $(R^1)(R^2)(R^3)Si-R^4-O-C(=O)-O-R^4-Si(R^1)(R^2)(R^3)$ are prepared by reaction of a silyl-substituted alcohol of Formula (II): $(R^1)(R^2)(R^3)Si-R^4-OH$ with an activated carbonyl compound of Formula (III): $C(=O)Z_2$ in the presence of a catalyst (e.g., an bicyclic amidine, a bicyclic guanidine, or a phosphazene) in an aprotic solvent. In Formulas (I) and (II) each of $R^1$ and $R^2$ independently is alkyl; $R^3$ is alkyl or $-X^1-Si(R^5)(R^6)(R^7)$; $X^1$ is O or alkylene; $R^4$ is alkylene; and each $R^5$, $R^6$, and $R^7$ independently is alkyl. In Formula (III), Z is 1-N-imidazolyl or 1-N-succinimidyl. In some embodiments, the catalyst used in the methods described herein comprises at least one base selected from the group consisting of a bicyclic amidine and a bicyclic guanidine. The reaction proceeds readily under both bulk and continuous flow reactor conditions.

21 Claims, 4 Drawing Sheets

METHOD FOR PREPARING BIS-(SILYLALKYL)CARBONATE ESTERS

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

This invention relates to silicon-containing dialkyl carbonate esters, such as bis-(silylalkyl)carbonates, which are useful, e.g., in non-aqueous solvents and electrolytes for electrochemical cells and batteries. More particularly, this invention relates to a method for preparing bis-(silylalkyl) carbonate esters.

BACKGROUND

Silicon-containing dialkyl carbonate ester compounds have been found to be useful as electrolyte solvents for non-aqueous electrochemical cells and batteries (e.g., lithium batteries) are described herein. The use of high-voltage, high-capacity positive electrodes in lithium-ion batteries is complicated by their tendency to degrade organic electrolyte solvents. Additionally, organic electrolyte solvents can have flammability issues, particularly when the batteries are subjected to excessive temperatures. Additives to improve thermal stability have been proposed for lithium batteries, as have flame resistant solvents. Various additives have been proposed that limit flame propagation or have flame retardant properties. Generally, these additives decrease the performance of the cell. The trade-off of the flame-suppressant properties interfere with the general operation of the battery, resulting in a poor overall product.

There is an ongoing need for improved methods of preparing silicon-containing carbonate esters for use, e.g., in advanced electrolyte solvents having one or more properties such as a large electrochemical stability window, a high ionic conductivity with a very low electronic conductivity, a low vapor pressure and low viscosity over a broad temperature range, and a lower flammability (e.g., due to a higher flash point) than conventional carbonate solvents. The methods described herein address this ongoing need.

SUMMARY OF THE INVENTION

Bis-(silylalkyl)carbonate esters of Formula (I):

$$(R^1)(R^2)(R^3)Si\text{—}R^4\text{—}O\text{—}C(\!=\!O)\text{—}O\text{—}R^4\text{—}Si(R^1)(R^2)(R^3) \quad (I)$$

are prepared by reaction of at least about two molar equivalents of a silyl-substituted alcohol of Formula (II): $(R^1)(R^2)(R^3)Si\text{—}R^4\text{—}OH$ with about one molar equivalent of an activated carbonyl compound of Formula (III): $C(\!=\!O)Z_2$ in the presence of a catalyst (e.g., an bicyclic amidine, a bicyclic guanidine, or a phosphazene) in an aprotic solvent. In Formulas (I) and (II) each of $R^1$ and $R^2$ independently is alkyl; $R^3$ is alkyl or $\text{—}X^1\text{—}Si(R^5)(R^6)(R^7)$; $X^1$ is O or alkylene; $R^4$ is alkylene; and each $R^5$, $R^6$, and $R^7$ independently is alkyl. In Formula (III), Z is 1-N-imidazolyl or 1-N-succinimidyl. In some embodiments, the catalyst used in the methods described herein comprises at least one base selected from the group consisting of a bicyclic amidine and a bicyclic guanidine. The reaction proceeds readily under both bulk and continuous flow reactor conditions.

A typical batch reaction involves adding a solution of about two equivalents of the silyl-substituted alcohol of Formula (II) in an aprotic solvent (e.g., acetonitrile) to a stirring solution or suspension of the about one equivalent of the activated carbonyl compound of Formula (III) and the catalyst in the same solvent at ambient room temperature. The stirring is continued until the reaction is complete (e.g., until the silyl-substituted alcohol, the activated carbonyl compound, or both, are no longer detected (e.g., by gas chromatography, liquid chromatography, or thin-layer chromatography), or until production of the product compound of Formula (I) ceases). Typically, after removal of at least some of the reaction solvent (e.g. by distillation, vacuum distillation, or rotatory evaporation), at least some byproducts of the reaction (e.g., imidazole) are removed by washing with an aqueous solvent, which also can remove some or most of the reaction solvent (e.g., if the reaction solvent is water-soluble or water-miscible). The resulting crude bis-(silylalkyl)carbonate ester of Formula (I) can then be purified, e.g., by distillation.

The compounds of Formula (I) described herein have good solubilizing properties for salts commonly used in lithium battery electrolytes, as well as excellent chemical compatibility and electrochemical stability properties. Batteries utilizing the bis-(silylalkyl)carbonates of Formula (I) as electrolyte solvents provide capacities similar to batteries using a conventional 3:7 (w/w) solvent mixture of ethylene carbonate and methyl ethyl carbonate, respectively (also known as Gen2 solvent), and exhibit coulombic efficiencies near 100%, when evaluated in a lithium-ion battery with 1.0 M $LiPF_6$ as the electrolyte salt, a graphite-based anode, and a lithium nickel-cobalt-manganese dioxide-based cathode.

In one example, bis-(trimethylsilylmethyl)carbonate has been synthesized by the methods described herein. A mixture of about two equivalents of trimethylsilyl methanol and one equivalent of carbonyldiimidazole (CDI) in acetonitrile forms a mono-substituted intermediate (see Scheme 1), which is substantially unreactive toward further displacement of imidazole by the trimethylsilylmethanol, even with prolonged heating. Including a simple base such as solid potassium hydroxide leads to formation of some desired product, but in relatively low yield (less than 50%) and at very slow reaction rates. Surprisingly, adding an organosuperbase catalyst (e.g., DBU or TBD), as described herein, facilitates complete displacement of both imidazole groups from CDI at room temperature (see Scheme 2).

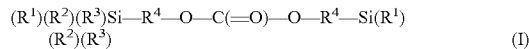

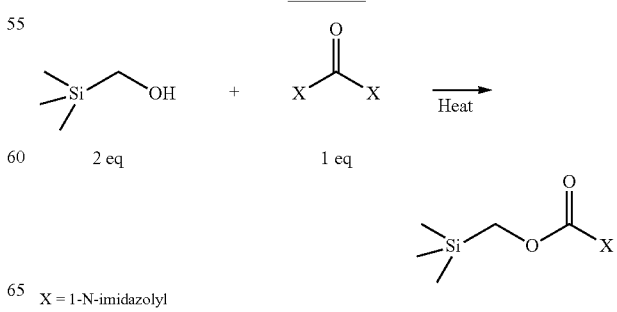

X = 1-N-imidazolyl

Scheme 2.

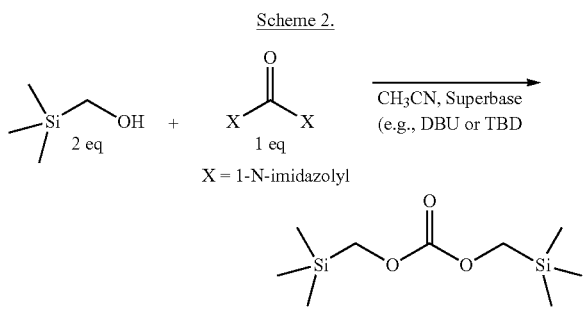

As another comparison, preparation of bis-(trimethylsilylmethyl) carbonate by an earlier reported method (which involved heating a mixture of dimethyl carbonate (DMC) and trimethylsilyl methanol in toluene in the presence of potassium phosphate catalyst) required heating at about 80-85° C. for about 24 hours (h), followed by distillation at 60 Torr without removal of the catalyst (see Scheme 3). Thus, the methods described herein provide a convenient and less expensive alternative to the earlier reported methods for preparing bis(silylalkyl) carbonates.

Scheme 3.

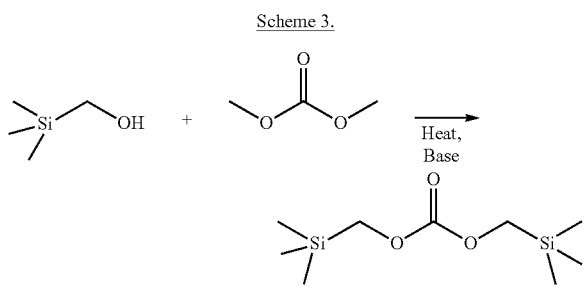

The following non-limiting embodiments of the methods described herein are provided below to illustrate certain aspects and features of the present invention.

Embodiment 1 comprises a method of preparing a bis-(silylalkyl)carbonate of Formula (I): $(R^1)(R^2)(R^3)Si\text{—}R^4\text{—}O\text{—}C(\text{=}O)\text{—}O\text{—}R^4\text{—}Si(R^1)(R^2)(R^3)$; the method comprising the sequential steps of: (a) contacting at least about two molar equivalents of silyl-substituted alcohol of Formula (II): $(R^1)(R^2)(R^3)Si\text{—}R^4\text{—}OH$ with about 1 molar equivalent of an activated carbonyl compound of Formula (III): $C(\text{=}O)Z_2$ in the presence of a catalyst in an aprotic solvent; and (b) isolating the bis-(silylalkyl)carbonate of Formula (I) from the solvent; wherein: the catalyst comprises at least one material selected from the group consisting of a bicyclic amidine base, a bicyclic guanidine base, and a phosphazene base; each of $R^1$ and $R^2$ independently is alkyl; $R^3$ is alkyl or $\text{—}X^1\text{—}Si(R^5)(R^6)(R^7)$; $X^1$ is 0 or alkylene; $R^4$ is alkylene; each of $R^5$, $R^6$, and $R^7$ independently is alkyl; and Z is 1-N-imidazolyl or 1-N-succinimidyl (i.e., wherein the compound of Formula (III) is carbonyldiimidazole or carbonyldisuccinimide).

Embodiment 2 comprises the method of Embodiment 1, wherein each of $R^1$ and $R^2$ independently is $C_1$ to $C_6$ alkyl.

Embodiment 3 comprises the method of Embodiment 1 or 2, wherein each of $R^1$ and $R^2$ is methyl.

Embodiment 4 comprises the method of any one of Embodiments 1 to 3, wherein $R^4$ is $C_1$ to $C_6$ alkylene (e.g., methylene).

Embodiment 5 comprises the method of any one of Embodiments 1 to 4, wherein $R^3$ is methyl.

Embodiment 6 comprises the method of any one of Embodiments 1 to 5, wherein $R^3$ is $\text{—}X^1\text{—}Si(R^5)(R^6)(R^7)$ and each of $R^5$, $R^6$, and $R^7$ independently is $C_1$ to $C_6$ alkyl.

Embodiment 7 comprises the method of any one of Embodiments 1 to 6, wherein each of $R^5$, $R^6$, and $R^7$ is methyl.

Embodiment 8 comprises the method of any one of Embodiments 1 to 7, wherein $X^1$ is $C_1$ to $C_6$ alkylene.

Embodiment 9 comprises the method of any one of Embodiments 1 to 8, wherein $X^1$ is $\text{—}CH_2\text{—}$.

Embodiment 10 comprises the method of any one of Embodiments 1 to 9, wherein Z is 1-N-imidazolyl.

Embodiment 11 comprises the method of any one of Embodiments 1 to 10, wherein the catalyst comprises: (a) a bicyclic amidine base selected from the group consisting of 1,8-diazabicyclo[5.4.0]undec-7-ene (DBU), 1,5-diazabicyclo[4.3.0]non-5-ene (DBN), and 1,5-diazabicyclo[4.4.0]dec-5-ene (DBD); (b) a bicyclic guanidine base selected from the group consisting of 1,5,7-triazabicyclo[4.4.0]dec-5-ene (TBD), 7-methyl-1,5,7-triazabicyclo-[4.4.0]dec-5-ene (MTBD), 7-ethyl-1,5,7-triazabicyclo-[4.4.0]dec-5-ene (ETBD), and 7-isopropyl-1,5,7-triazabicyclo-[4.4.0]dec-5-ene (ITBD); or a combination of (a) and (b).

Embodiment 12 comprises the method of any one of Embodiments 1 to 11, wherein the catalyst comprises at least one base selected from the group consisting of TBD and DBU.

Embodiment 13 comprises the method of any one of Embodiments 1 to 12, wherein the aprotic solvent comprises at least one solvent selected from the group consisting of an ether, a nitrile, an ester, and organic carbonate ester, an amide, a ketone, a sulfone, a sulfoxide, a hydrocarbon, and a halogenated hydrocarbon.

Embodiment 14 comprises the method of any one of Embodiments 1 to 13, wherein the aprotic solvent comprises acetonitrile.

Embodiment 15 comprises the method of any one of Embodiments 1 to 14, wherein each of each of $R^1$, $R^2$, and $R^3$ is methyl; $R^4$ is $\text{—}CH_2\text{—}$; and Z is 1-N-imidazolyl.

Embodiment 16 comprises the method of any one of Embodiments 1 to 15, wherein the solvent comprises acetonitrile; and the catalyst comprises DBU or TBD.

Embodiment 17 comprises the method of any one of Embodiments 1 to 16, wherein the contacting step (a) is performed at a temperature in the range of about 0 to about 180° C. (e.g., 20 to 120° C.).

Embodiment 18 comprises the method of any one of Embodiments 1 to 17, wherein the contacting step (a) is performed over a time period in the range of about 1 to about 24 hours.

Embodiment 19 comprises the method of any one of Embodiments 1 to 18, wherein the contacting step is performed in a heated continuous flow reactor at a temperature in the range of about 20 to about 180° C. (e.g., 40 to 160° C.) with a residence time within the heated continuous flow reactor in the range of about 0.1 to about 8 minutes (e.g., 0.5 to 6 minutes).

Embodiment 21 comprises the method of any one of Embodiments 1 to 19, wherein each of each of $R^1$, $R^2$, and $R^3$ is methyl; $R^4$ is $\text{—}CH_2\text{—}$; and Z is 1-N-imidazolyl.

Embodiment 21 comprises the method of any one of Embodiments 1 to 20, wherein the solvent comprises acetonitrile; and the catalyst comprises DBU or TBD.

Embodiment 22 comprises the method of any one of Embodiments 1 to 21, wherein the compound of Formula (II) is present in the aprotic solvent at a concentration of about 0.1 to about 6 M, and the activated carbonyl compound is present in the aprotic solvent at a concentration of about 0.1 to about 2 M.

Embodiment 23 comprises the method of any one of Embodiments 1 to 22, wherein the catalyst is present in the aprotic solvent at a concentration of about 0.5 to about 25 mol % (e.g., 1 to 20 mol %) relative to the concentration of the compound of Formula (II).

DETAILED DESCRIPTION

Figure 1:
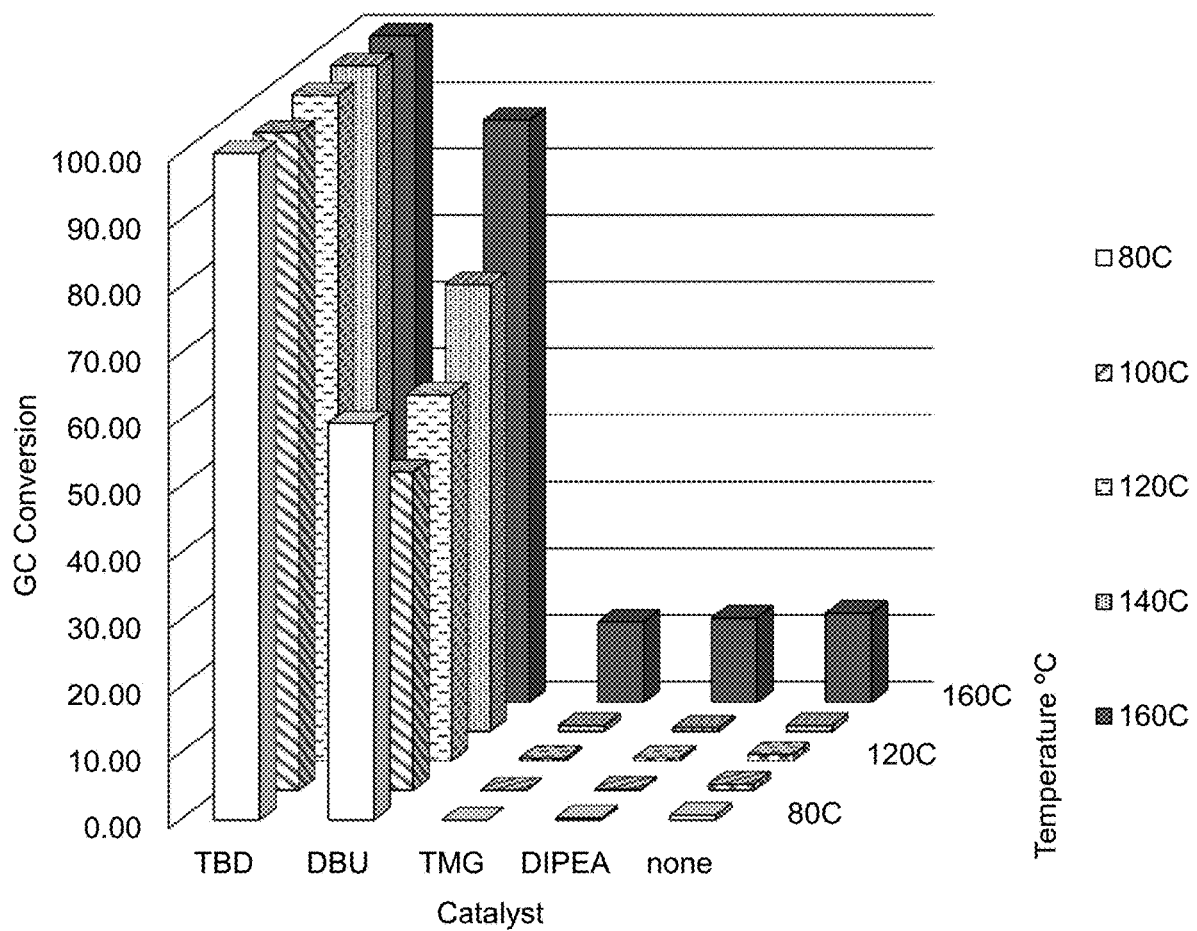
FIG. 1 shows plots of % conversion (vertical axis) for reaction of trimethylsilylmethanol (TMSM) and carbonyldiimidazole (CDI) for reactions with various catalysts at various temperatures in a continuous flow reactor system in acetonitrile solvent.

Bis-(silylalkyl)carbonate esters of Formula (I):

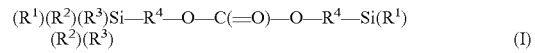

$(R^1)(R^2)(R^3)Si-R^4-O-C(=O)-O-R^4-Si(R^1)(R^2)(R^3)$ (I)

are prepared by reaction of a silyl-substituted alcohol of Formula (II): $(R^1)(R^2)(R^3)Si-R^4-OH$ with an activated carbonyl compound of Formula (III): $C(=O)Z_2$ (e.g., carbonyldiimidazole) in the presence of an organosuperbase catalyst (e.g., an bicyclic amidine, a bicyclic guanidine, a phosphazene; and the like) in an aprotic solvent. In Formula (I) and Formula (II), each of $R^1$ and $R^2$ independently is alkyl (e.g., each can be the same or a different $C_1$ to $C_6$ alkyl, such as methyl, ethyl, tert-butyl, and the like); $R^3$ is alkyl (e.g., $C_1$ to $C_6$ alkyl) or $-X^1-Si(R^5)(R^6)(R^7)$; $X^1$ is O or alkylene (e.g., $C_1$ to $C_6$ alkylene, such as $-CH_2-$, $-CH_2CH_2-$, $-CH_2-CH(CH_3)-$, and the like); $R^4$ is alkylene (e.g., $C_1$ to $C_6$ alkylene); and each $R^5$, $R^6$, and $R^7$ independently is alkyl (e.g., each can be the same or a different $C_1$ to $C_6$ alkyl). In Formula (III), Z is 1-N-imidazolyl or 1-N-succinimidyl. Preferably, the catalyst used in the methods described herein comprises at least one base selected from the group consisting of a bicyclic amidine and a bicyclic guanidine. The reaction proceeds readily under both bulk and continuous flow reactor conditions.

A typical batch reaction involves adding a solution of a silyl-substituted alcohol of Formula (II) in an aprotic solvent (e.g., acetonitrile) to a stirring solution or suspension of the activated carbonyl compound of Formula (III) and the catalyst in the same solvent at ambient room temperature. The stirring is continued until the reaction is complete (e.g., until the silyl-substituted alcohol, the activated carbonyl compound, or both, are no longer detected (e.g., by gas chromatography, liquid chromatography, or thin-layer chromatography), or until production of the product compound of Formula (I) ceases). Typically, after removal of at least some of the reaction solvent (e.g. by distillation, vacuum distillation, or rotatory evaporation), at least some byproducts of the reaction (e.g., imidazole) typically are removed by washing with an aqueous solvent, which also can remove some or most of the reaction solvent (e.g., if the reaction solvent is water-soluble or water-miscible). The resulting crude bis-(silylalkyl)carbonate ester of Formula (I) can then be purified, e.g., by distillation.

Also described herein is a continuous process for manufacturing a compound of Formula (I). The process involves simultaneously pumping a first solution comprising of a silyl alcohol of Formula (II) and the catalyst in a first solvent, and a second solution of the activated carbonyl compound of Formula (III) in a second solvent through a heated continuous flow-reactor vessel where the first and second solutions mix together, optionally with in-line active or static mixing, at a temperature in the range of about 0 to about 180° C., and then collecting an effluent comprising the compound of Formula (I) exiting from the heated vessel. Solvent is then removed from the effluent (e.g., by evaporation or washing with an aqueous solvent) and the resulting crude product of Formula (I) is isolated and purified by distillation. The heated vessel typically is either a glass micro-reactor or a tube (e.g., a coil of tubing) within a heating chamber (e.g., a furnace or heating bath, or a tube that includes one or more heating elements (e.g., heating tape) in contact with the tube. Preferably, the mixed solutions have a residence time of about 0.1 to about 8 minutes within the heated reactor vessel. The vessel includes an opening (e.g., the other end of the tube from where the solution are being pumped) that allows the mixed solutions to exit the heated vessel for collection. As the solutions are continuously pumped together into and through the vessel, the effluent containing the product continuously flows out of the vessel for collection.

The temperature and residence time within a heated portion of the reactor are selected so that the reaction is substantially complete when by the time the reaction mixture flows out of the heated portion of the reactor. The completeness of the reaction can be monitored by, e.g., by gas chromatography, liquid chromatography, or thin-layer chromatography to determine when the silyl-substituted alcohol, the activated carbonyl compound, or both, are no longer detected, or when production of the product compound of Formula (I) has ceased. At least some byproducts of the reaction (e.g., imidazole) typically are removed from the effluent by washing with an aqueous solvent, which also can remove some or most of the reaction solvent (e.g., if the reaction solvent is water-soluble or water-miscible). The resulting crude bis-(silylalkyl)carbonate ester of Formula (I) can then be purified, e.g., by distillation.

Non-limiting examples of bicyclic amidine catalysts include, e.g., 1,8-diazabicyclo[5.4.0]undec-7-ene (DBU), 1,5-diazabicyclo[4.3.0]non-5-ene (DBN), 1,5-diazabicyclo[4.4.0]dec-5-ene (DBD), and the like. Non-limiting examples of bicyclic guanidine catalysts include, e.g., 1,5,7-triazabicyclo[4.4.0]dec-5-ene (TBD), 7-methyl-1,5,7-triazabicyclo-[4.4.0]dec-5-ene (MTBD), 7-ethyl-1,5,7-triazabicyclo-[4.4.0]dec-5-ene (ETBD), 7-isopropyl-1,5,7-triazabicyclo-[4.4.0]dec-5-ene (ITBD), and the like. Non-limiting examples of phosphazene catalysts include, e.g., 2-tert-butylimino-2-diethylamino-1,3-dimethylperhydro-1,3,2-diazaphosphorine (BEMP), 1-tert-butyl-4,4,4-tris-(dimethylamino)-2,2-bis[tris(dimethylamino)-phosphoranylidenamino]-$2\lambda^5,4\lambda^5$-catenadi(phosphazene) ($P_4$-t-Bu), and the like. In some embodiments, two or more of the catalysts can be used together. A preferred bicyclic amidine catalyst is DBU. A preferred bicyclic guanidine catalyst is TBD.

The catalyst typically is utilized in batch reactions at a concentration of about 1 to about 20 mol %, preferably about 5 to about 10 mol %, based on the concentration of the compound of Formula II. In a batch process, the catalyst preferably is present at a concentration of about 1 to about 10 mol %. If desired, the reaction can be carried out in a continuous flow reactor, in which case the catalyst can be included in either the first or second solution, and is present in the combined solutions in the continuous flow reactor at a concentration of about 1 to about 20 mol %.

A typical batch reaction is run at a temperature of about ambient room temperature (e.g., about 20° C.) to about 80° C., preferably about 20 to about 40° C. A typical continuous flow reaction is run at a temperature of 20 to about 180° C., preferably about 40 to about 100° C.

In batch reactions, the concentration of the silyl-substituted alcohol in the aprotic solvent typically is in the range of about 0.5 to about 4 M, preferably about 1 M to about 2 M; and the concentration of the activated carbonyl compound typically is in the range of about 0.1 to about 2 M, preferably about 0.5 to about 1 M. The silyl-substituted alcohol can be added neat or as a solution in the reaction solvent (e.g., acetonitrile).

Solvents that are useful in the methods described herein are aprotic organic solvents, such as ethers, nitriles, esters, organic carbonates, amides, ketones, sulfones, sulfoxides, hydrocarbons, and halogenated hydrocarbons. In some embodiments, polar aprotic solvents are preferred (e.g., tetrahydrofuran (THF), acetonitrile, N,N-dimethylformamide (DMF), sulfolane, dimethylsulfoxide, and the like).

Non-limiting examples of suitable ether solvents include diethylether, THF, 1,3-dioxolane, dioxane, dimethoxyethane (DME or glyme), bis(2-methoxyethyl) ether (diglyme), and the like. Non-limiting examples of suitable nitrile solvents include acetonitrile, propionitrile, butyronitrile, and the like. Non-limiting examples of suitable ester solvents include methyl acetate, ethyl acetate, propyl acetate, isobutyl acetate, ethyl butyrate, methyl propionate, and the like. Non-limiting examples of suitable organic carbonate solvents include ethylene carbonate (EC), propylene carbonate (PC), dimethyl carbonate, ethyl methyl carbonate, and the like. Non-limiting examples of suitable amide solvents include DMF, N,N-dimethylacetamide (DMAc), N-methylpyrrolidone (NMP), and the like. Non-limiting examples of suitable ketone solvents include acetone, methyl ethyl ketone (MEK), and the like. Non-limiting examples of suitable sulfone solvents include dimethylsulfone, sulfolane, and the like. A non-limiting example of a suitable sulfoxide solvents is dimethylsulfoxide. Non-limiting examples of suitable hydrocarbon solvents include aromatic hydrocarbons such as benzene, toluene, xylenes, and the like, as well as aliphatic hydrocarbons such as pentane, hexane, and the like. Non-limiting examples of suitable halogenated hydrocarbon solvents include aliphatic halogenated hydrocarbons such as dichloromethane (methylene chloride, trichloromethane (chloroform), hexachloroethane (perchloroethane), perfluoroalkanes, and the like; and aromatic halogenated hydrocarbons such as o-dichlorobenzene, m-dichlorobenzene, p-dichlorobenzene, 1,2,3-trichlorobenzene, 1,3,5-trichlorobenzene, 1,2,4-trichlorobenzene, hexachlorobenzene, 1-chloro-3-nitrobenzene, 1-bromo-4-chlorobenzene, and the like. In some embodiments, the preferred solvents include acetonitrile, DMSO, DMF, MTBE, toluene, dimethyl carbonate, and diethyl carbonate.

As used in reference to the methods described herein, the term "solution" refers to liquid compositions in which a material is dissolved in a solvent, as well as to liquid suspensions in which include a solid material suspended in a liquid vehicle. In such suspensions, the solid material may be partially or completely insoluble in the liquid vehicle. For convenience, the term "solvent" as used herein is to be construed as synonymous with the term "liquid vehicle".

As used herein, the term "alkyl" and grammatical variations thereof refers to a univalent saturated hydrocarbon group, i.e., saturated hydrocarbon lacking one hydrogen atom, e.g. methyl, ethyl, propyl, isopropyl, butyl, 1-methyl-1-propyl (also known as sec-butyl), 2-methyl-1-propyl (also known as isobutyl), pentyl, hexyl, cyclopenyl, cyclohexyl, and the like. Alkyl groups can include linear chains of carbons atoms (linear alkyl), branched chains of carbon atoms (branched alkyl), rings of carbon atoms (e.g., cycloalkyl), or any combination thereof. In some embodiments of the compounds of Formula (I) and (II) an alkyl group can comprise 1 to 6 carbon atoms (also referred to as "$C_1$ to $C_6$ alkyl"), such as methyl, ethyl, propyl, and the like. In some embodiments, preferred alkyl groups include methyl and ethyl.

As used herein the term "alkylene" refers to a bivalent saturated aliphatic radical (e.g., such as ethylene ($—CH_2CH_2—$), propylene ($—CH_2CH_2CH_2—$), and the like), which is formally regarded as derived from an alkene by opening of the double bond or from an alkane by removal of two hydrogen atoms from different carbon atoms. In some embodiments of the compounds of Formula (I) and (II) an alkylene group can comprise 1 to 6 carbon atoms (also referred to as "$C_1$ to $C_6$ alkylene"), such as methylene ($—CH_2—$), ethylene ($—CH_2CH_2—$), linear propylene (e.g., $—CH_2CH_2CH_2—$), branched propylene (e.g., $—CH_2(CH_3)CH_2—$), and the like.

The following non-limiting Examples are provided to illustrate certain features of the compositions and methods described herein.

Example 1. Continuous Flow Reaction Preparation of Bis-(trimethylsilyl)methyl Carbonate (BTMSMC) with Cyclic Guanidine and Amidine Catalysts

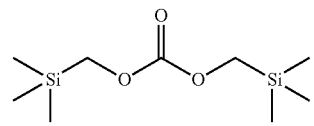

Four solutions of trimethylsilylmethanol (TMSM) in acetonitrile (MeCN; 0.5 M) containing 10 mol % of base catalysts (TBD, DBU, tetramethylguanidine (TMG), and diisopropylethylamine (DIPEA), were prepared, as well as one solution with TMSM alone (0.5 M in MeCN). CDI solutions in MeCN (0.5 M) were also prepared. These solutions were used in a SYRRIS continuous flow cell reactor system. The flow cell was a microchip with a 1 mL volume flow channel within a chip heater. The CDI and individual TMSM solutions were simultaneously pumped through the heated channel of the reactor. The reaction pressure (resulting from the pumping flow rate through the channel of the microchip) was set to 8 bar, the residence time was 4 minutes, and temperature was varied (80, 100, 120, 140, and 160° C.). TMSM was used in 2.1 mole equivalents relative to CDI. Reaction conversion of intermediate mono-substituted imidazolyl-C(O)—$OCH_2SiMe_3$ to BTMSMC was varied (see FIG. 1), with bicyclic guanidine catalyst (TBD) showing complete conversion at all temperatures, and bicyclic amidine catalyst (DBU) showing relatively high activity, while the noncyclic guanidine (TMG) and the simple tertiary amine (DIPEA) catalysts were essentially inactive until the reaction temperature was raised to about 160° C., at which time a low conversion to BTMSMC of about 10% was observed.

As a comparison, the reactions with DIPEA and no catalyst were repeated in both MeCN and DMF. Solutions of TMSM in MeCN (1 M) and DMF (2 M) were prepared. CDI solutions in MeCN (0.5 M) and DMF (1 M) were also prepared. These solutions were used in a SYRRIS continuous flow cell reactor system. The flow cell was a microchip with a 1 mL volume flow channel within a chip heater. Reaction pressure was varied from 12 to 15 bar depending on temperature (120, 140, 160 and 180° C.). TMSM was used in 2.2 mole equivalents relative to CDI. Reaction conversion of intermediate to BTMSMC was poor at about 20% (see FIG. 2). CDI was not substantially present in the GC, so conversion numbers are proportionate to the major product, which was the mon-substituted imidazolyl-C(O)—OCH$_2$SiMe$_3$ "intermediate". The reaction product was analyzed by GC/MS. Severe decomposition was noted at higher temperatures, particularly in DMF. This experiment was repeated with 10 mol % DIPEA added to the TMDM solutions. The results are shown in FIG. 3.

Figure 2:
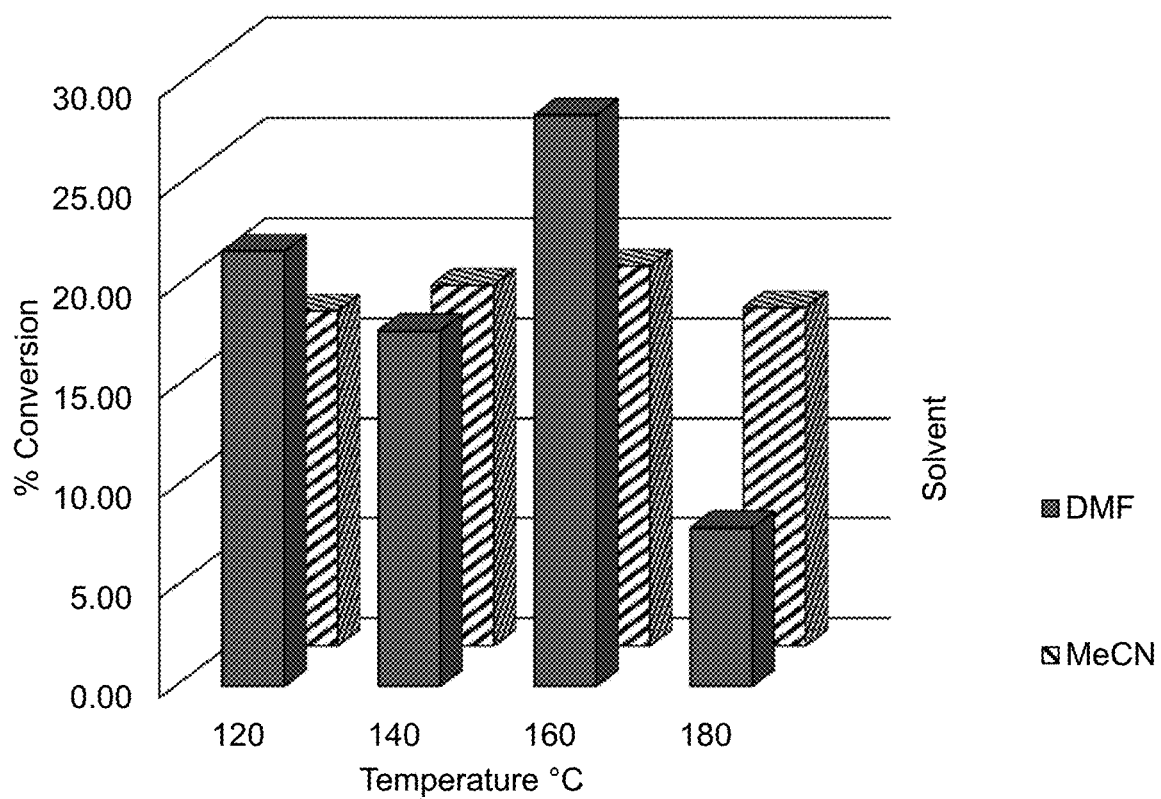
FIG. 2 shows plots of % conversion (vertical axis) for reaction of TMSM with CDI in the absence of catalyst at various temperatures in a continuous flow reactor system in acetonitrile and dimethylformamide solvents.
Figure 3:
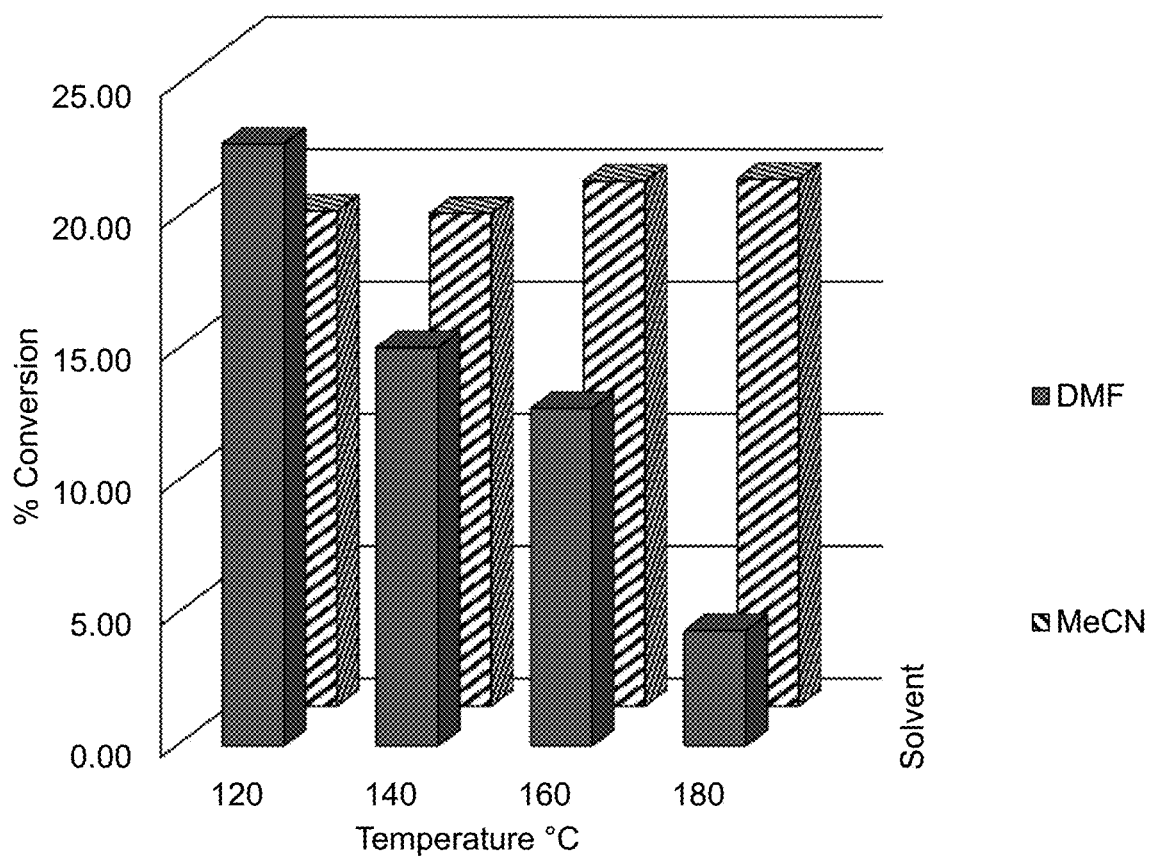
FIG. 3 shows plots of % conversion (vertical axis) for reaction of TMSM and CDI in the presence of diisopropylethylamine catalyst at various temperatures in a continuous flow reactor system in acetonitrile and dimethylformamide solvents.

As is evident from FIG. 2 and FIG. 3, the conversions to BTMSMC were low, with the major product of these reactions being the mono-substituted imidazolyl-C(O)—OCH$_2$SiMe$_3$.

Example 2. Batch Preparation BTMSMC—Small Scale

For screening purposes, four reaction vials were charged with CDI, solvent (acetonitrile or methyltertbutylether (MTBE)) and trimethylsilylmethanol. The reactions were stirred for about 30 minutes at room temperature, and analyzed by GC/MS, showing all reactions had progressed to the imidazolyl-C(O)—OCH$_2$SiMe$_3$ intermediate. At 30 minutes, base catalysts (KOH or DBU) were added. The reactions were followed by GC/MS, measuring conversion from the intermediate to BTMSMC. After 4 hours, both vials B and C had substantial solids present in the reaction mixtures (Table 1). Vial A was essentially unreacted, leaving vial D as the only suitable combination of solvent and catalyst under these conditions, particularly for use in a continuous flow system, which requires absence of solids in the reaction (Table 1).

Figure 4:
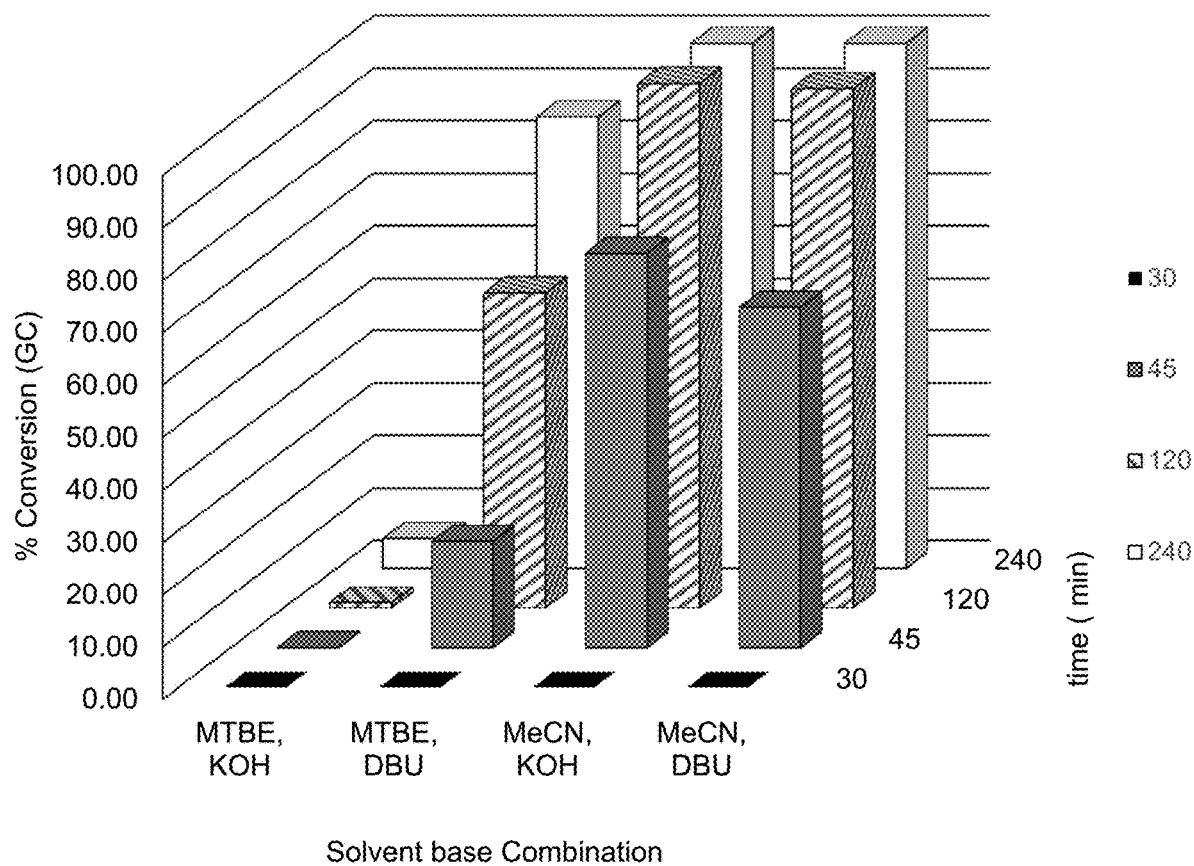
FIG. 4 shows plots of % conversion (vertical axis) for batch reactions of TMSM and CDI with various base catalyst and solvent combinations at various reaction times.

Quantitative results are shown in FIG. 4.

TABLE 1

| Reaction Vial | Solvent | Base | 2 Hour Reaction Time? | Solution Formed? | Suitable For Flow Reaction? |
| --- | --- | --- | --- | --- | --- |
| A | MTBE | KOH | No | Yes | No |
| B | MTBE | DBU | Some | No | No |
| C | MeCN | KOH | Yes | No | No |
| D | MeCN | DBU | Yes | Yes | Yes |

Example 3. Scale-Up Preparation BTMSMC

A 1-L 3-neck round bottom flask was charged with MeCN (200 mL) and purged with nitrogen. Magnetic stirring was started, and CDI (78.45 g) was added, followed by a second charge of MeCN (200 mL). DBU (5 mL) was charged to the resulting slurry. TMSM (100.03 g) was added at about 1.0 mL/min via a peristaltic pump, causing the final temperature of the reaction to rise from about 22° C. to 31° C. After about 1 hour, the GC analysis showed the reaction was complete. The solution was then concentrated by rotary evaporation, and the residue was partitioned between MTBE (400 mL) and water (100 mL). After separation of the MTBE phase and drying with sodium sulfate, the MTBE was removed on the rotary evaporator. The resulting oily residue was vacuum distilled. GC analysis showed some co-distillation of the imidazole byproduct. Because of this, the product re-dissolved in heptane and washed with water, 1% HCl, water, and saturated brine to remove residual imidazole. Workup as above, followed by distillation provided pure (>99.5% by GC) BTMSMC product in 75% yield.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The terms "consisting of" and "consists of" are to be construed as closed terms, which limit any compositions or methods to the specified components or steps, respectively, that are listed in a given claim or portion of the specification. In addition, and because of its open nature, the term "comprising" broadly encompasses compositions and methods that "consist essentially of" or "consist of" specified components or steps, in addition to compositions and methods that include other components or steps beyond those listed in the given claim or portion of the specification. Recitation of ranges of values herein are merely intended to serve as a shorthand method of referring individually to each separate value falling within the range, unless otherwise indicated herein, and each separate value is incorporated into the specification as if it were individually recited herein. All numerical values obtained by measurement (e.g., weight, concentration, physical dimensions, removal rates, flow rates, and the like) are not to be construed as absolutely precise numbers, and should be considered to encompass values within the known limits of the measurement techniques commonly used in the art, regardless of whether or not the term "about" is explicitly stated. All methods described herein can be performed in any suitable order unless otherwise indicated herein or otherwise clearly contradicted by context. The use of any and all examples, or exemplary language (e.g., "such as") provided herein, is intended merely to better illuminate certain aspects of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to The embodiments of the invention in which an exclusive property or privilege is claimed are defined as follows:

1. A method of preparing a bis-(silylalkyl)carbonate of Formula (I):
$(R^1)(R^2)(R^3)Si-R^4-O-C(=O)-O-R^4-Si(R^1)(R^2)(R^3)$; the method comprising the sequential steps of:
  (a) contacting at least about two molar equivalents of silyl-substituted alcohol of Formula (II): $(R^1)(R^2)(R^3)Si-R^4-OH$ with about 1 molar equivalent of an activated carbonyl compound of Formula (III): $C(=O)Z_2$ in the presence of a catalyst in an aprotic solvent; and
  (b) isolating the bis-(silylalkyl)carbonate of Formula (I) from the solvent;
  wherein:
  the catalyst comprises at least one material selected from the group consisting of a bicyclic amidine base, a bicyclic guanidine base, and a phosphazene base;
  each of $R^1$ and $R^2$ independently is alkyl;
  $R^3$ is alkyl or $-X^1-Si(R^5)(R^6)(R^7)$;
  $X^1$ is O or alkylene;
  $R^4$ is alkylene;
  each of $R^5$, $R^6$, and $R^7$ independently is alkyl; and
  Z is 1-N-imidazolyl or 1-N-succinimidyl.

2. The method of claim 1, wherein each of $R^1$ and $R^2$ independently is $C_1$ to $C_6$ alkyl.

3. The method of claim 1, wherein each of $R^1$ $R^2$, and $R^3$ is methyl.

4. The method of claim 1, wherein $R^4$ is $-CH_2-$.

5. The method of claim 2, wherein $R^3$ is methyl.

6. The method of claim 2, wherein $R^3$ is $-X^1-Si(R^5)(R^6)(R^7)$ and each of $R^5$, $R^6$, and $R^7$ independently is $C_1$ to $C_6$ alkyl.

7. The method of claim 6, wherein each of $R^5$, $R^6$, and $R^7$ is methyl.

8. The method of claim 6, wherein $X^1$ is $C_1$ to $C_6$ alkylene.

9. The method of claim 6, wherein $X^1$ is $-CH_2-$.

10. The method of claim 1, wherein Z is 1-N-imidazolyl.

11. The method of claim 1, wherein the catalyst comprises:
  (a) a bicyclic amidine base selected from the group consisting of 1,8-diazabicyclo[5.4.0]undec-7-ene (DBU), 1,5-diazabicyclo[4.3.0]non-5-ene (DBN), and 1,5-diazabicyclo[4.4.0]dec-5-ene (DBD);
  (b) a bicyclic guanidine base selected from the group consisting of 1,5,7-triazabicyclo[4.4.0]dec-5-ene (TBD), 7-methyl-1,5,7-triazabicyclo-[4.4.0]dec-5-ene (MTBD), 7-ethyl-1,5,7-triazabicyclo-[4.4.0]dec-5-ene (ETBD), and 7-isopropyl-1,5,7-triazabicyclo-[4.4.0]dec-5-ene (ITBD); or
  (c) a combination of (a) and (b).

12. The method of claim 1, wherein the catalyst comprises at least one base selected from the group consisting of TBD and DBU.

13. The method of claim 1, wherein the aprotic solvent comprises at least one solvent selected from the group consisting of an ether, a nitrile, an ester, and organic carbonate ester, an amide, a ketone, a sulfone, a sulfoxide, a hydrocarbon, and a halogenated hydrocarbon.

14. The method of claim 1, wherein the aprotic solvent comprises acetonitrile.

15. The method of claim 1, wherein each of each of $R^1$, $R^2$, and $R^3$ is methyl; $R^4$ is $-CH_2-$; and Z is 1-N-imidazolyl.

16. The method of claim 13, wherein the solvent comprises acetonitrile; and the catalyst comprises DBU or TBD.

17. The method of claim 1, wherein the contacting step (a) is performed at a temperature in the range of about 0 to about 180° C.

18. The method of claim 1, wherein the contacting step (a) is performed over a time period in the range of about 1 hour to about 24 hours.

19. The method of claim 1, wherein the contacting step is performed in a heated continuous flow reactor at a temperature in the range of about 20 to about 180° C. with a residence time within the heated continuous flow reactor in the range of about 0.1 to about 8 minutes.

20. The method of claim 1, wherein the compound of Formula (II) is present in the aprotic solvent at a concentration of about 0.1 to about 6 M, and the activated carbonyl compound is present in the aprotic solvent at a concentration of about 0.1 to about 2 M.

21. The method of claim 1, wherein the catalyst is present in the aprotic solvent at a concentration of about 0.5 to about 25 mol % relative to the concentration of the compound of Formula (II).

* * * * *